US012383919B2

United States Patent
Zhou et al.

(10) Patent No.: US 12,383,919 B2
(45) Date of Patent: Aug. 12, 2025

(54) ATOMIZING MODULE CAPABLE OF CHANGING FLUID SPEED AND FRAGRANCE DIFFUSER WITH THE MODULE

(71) Applicant: Shenzhen Natural Origin Living Science and Technology Co., Ltd., Guangdong (CN)

(72) Inventors: Danhua Zhou, Guangdong (CN); Liang You, Guangdong (CN)

(73) Assignee: Shenzhen Natural Origin Living Science and Technology Co., Ltd., Shenzhen (CN)

( * ) Notice: Subject to any disclaimer, the term of this patent is extended or adjusted under 35 U.S.C. 154(b) by 469 days.

(21) Appl. No.: 18/089,589

(22) Filed: Dec. 28, 2022

(65) Prior Publication Data
US 2024/0082862 A1    Mar. 14, 2024

(30) Foreign Application Priority Data
Sep. 13, 2022    (CN) .......................... 202211112086.8

(51) Int. Cl.
*B05B 12/00* (2018.01)
*A61L 9/14* (2006.01)

(52) U.S. Cl.
CPC ............ *B05B 12/0022* (2018.08); *A61L 9/14* (2013.01); *A61L 2209/12* (2013.01); *A61L 2209/132* (2013.01); *A61L 2209/134* (2013.01)

(58) Field of Classification Search
CPC .... B05B 12/0022; A61L 9/14; A61L 2209/12; A61L 2209/132; A61L 2209/134
See application file for complete search history.

(56) References Cited

FOREIGN PATENT DOCUMENTS

| CN | 211190745 U | 8/2020 | |
|---|---|---|---|
| WO | WO-2020119124 A1 * | 6/2020 | ............... A61L 9/14 |
| WO | WO-2021185081 A1 * | 9/2021 | ............... A61L 9/14 |

* cited by examiner

*Primary Examiner* — Sean E Conley

(57) ABSTRACT

An atomizing module includes an atomizing housing, a liquid guide piece and an atomizing sheet. The atomizing housing includes a mounting part and a buffering part, the buffering part connects the mounting part, the buffering part defines a liquid buffering cavity, the atomizing housing defines an air inlet channel, an atomizing cavity and a mist outlet, the atomizing cavity communicates with the air inlet channel, the mist outlet communicates with the atomizing cavity, and the buffering part extends into the atomizing cavity. The liquid guide piece is in the liquid buffering cavity and located at one end of the buffering part facing away from the mounting part, and the liquid guide piece slows down a dropping speed of liquid and control whether the liquid drops. The atomizing sheet is located on one side of the liquid guide piece facing away from the mounting part.

20 Claims, 9 Drawing Sheets

ATOMIZING MODULE CAPABLE OF CHANGING FLUID SPEED AND FRAGRANCE DIFFUSER WITH THE MODULE

CROSS-REFERENCE TO RELATED APPLICATIONS

The present disclosure claims priority of Chinese Patent Application No. 202211112086.8, filed on Sep. 13, 2022, titled "ATOMIZING MODULE CAPABLE OF CHANGING FLUID SPEED AND FRAGRANCE DIFFUSER WITH THE MODULE", the contents of which are incorporated herein by reference.

TECHNICAL FIELD

The present disclosure relates to the field of atomization, and particularly, relates to an atomizing module capable of changing fluid speed and an air conditioning equipment with the module.

BACKGROUND

At present, atomization equipment usually includes an atomizing module and a power supplying module which are connected with each other, the atomizing module is provided therein with a liquid storage cavity and an atomizing core, and the power supplying module is used for supplying power to the atomizing core, such that the atomizing core heats and atomizes the solution in the liquid storage cavity. Various kinds of electronic products use atomization equipment, such as electronic cigarettes, fragrance diffusers, atomization water tanks and other products.

The Chinese utility model patent with application No. 202021116156.3 discloses a liquid atomization unit which includes a housing, the housing defines an atomizing cavity therein, a mist outlet is arranged above the atomizing cavity, the housing defines an airflow channel at one side of the atomizing cavity, the airflow channel is used for introducing the airflow outside the housing, and the airflow goes through the airflow channel and then enters the atomizing cavity through an airflow outlet; a liquid retention cavity is further arranged between the airflow outlet and the airflow channel, and the liquid supplied through the liquid channel is stored in the liquid retention cavity; the airflow passes through the liquid retention cavity, such that the liquid is atomized to form atomized liquid, which enters the atomizing cavity through the airflow outlet and is atomized again in the atomizing cavity; the liquid atomization unit further includes a mist amount adjusting unit, which is arranged above the atomizing cavity and used for adjusting the mist amount exiting through the mist outlet.

In such an atomization unit, because the bottle is placed upright, the liquid at the bottom of the bottle cannot be fully atomized, and if the bottle is simply turned upside down, the speed of liquid flow and atomization amount cannot be controlled.

SUMMARY

An embodiment of the present disclosure provides an atomizing module which includes an atomizing housing, a liquid guide piece and an atomizing sheet. The atomizing housing includes a mounting part and a buffering part, the mounting part connects an external liquid bottle, the buffering part connects the mounting part, the buffering part defines a liquid buffering cavity, the atomizing housing defines an air inlet channel, an atomizing cavity and a mist outlet, the air inlet channel connects an external ventilation device, the atomizing cavity is in communication with the air inlet channel, the mist outlet is in communication with the atomizing cavity, and the buffering part extends into the atomizing cavity. The liquid guide piece is in the liquid buffering cavity and located at one end of the buffering part facing away from the mounting part, and the liquid guide piece slows down a dropping speed of liquid and control whether the liquid drops. The atomizing sheet is located on one side of the liquid guide piece facing away from the mounting part.

Another embodiment of the present disclosure provides a fragrance diffuser which includes a host housing, a micro blower, an electric control main board and the atomizing module as described above. The host housing defines a host chamber, the atomizing module is arranged in the host chamber, the micro blower and the electric control main board are both arranged in the host housing, an air outlet of the micro blower is in communication with the air inlet of the air inlet channel, the electric control main board is electrically connected with the atomizing sheet, and the electric control main board is configured to control the atomizing sheet to atomize the liquid.

DETAILED DESCRIPTION

Figure 1:
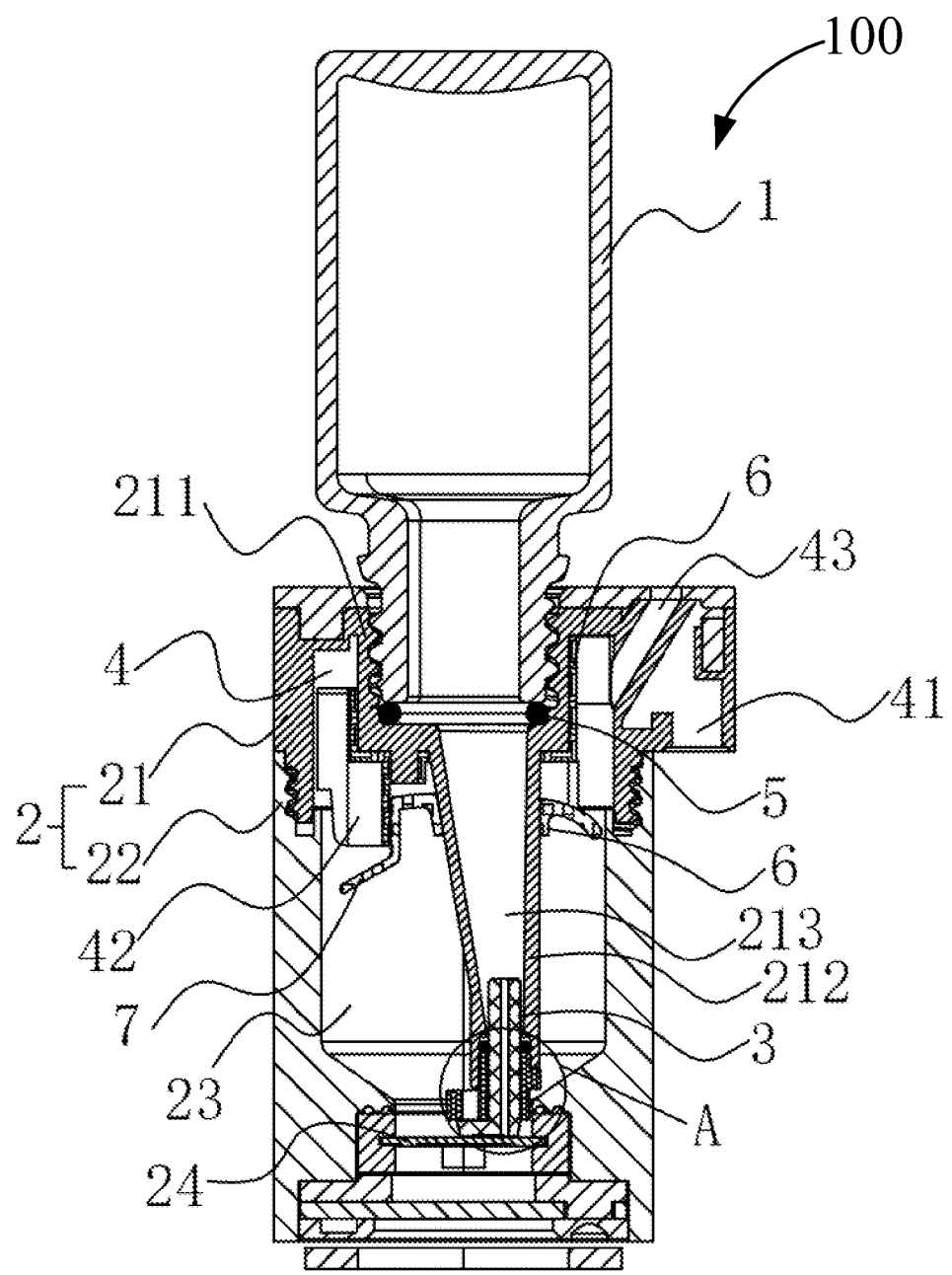
FIG. 1 is a schematic cross-sectional view of an atomizing module according to one embodiment of the present disclosure.
Figure 2:
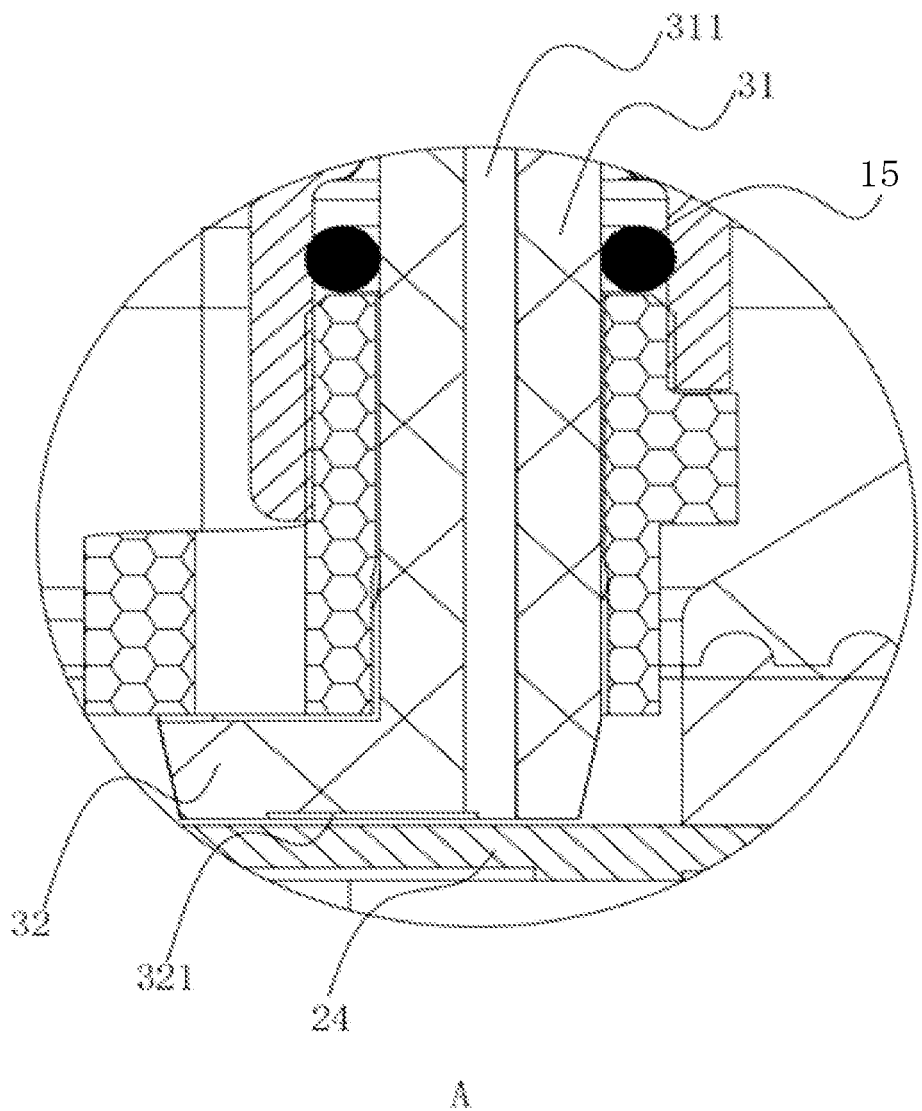
FIG. 2 is an enlarged view of a part A in FIG. 1.
Figure 3:
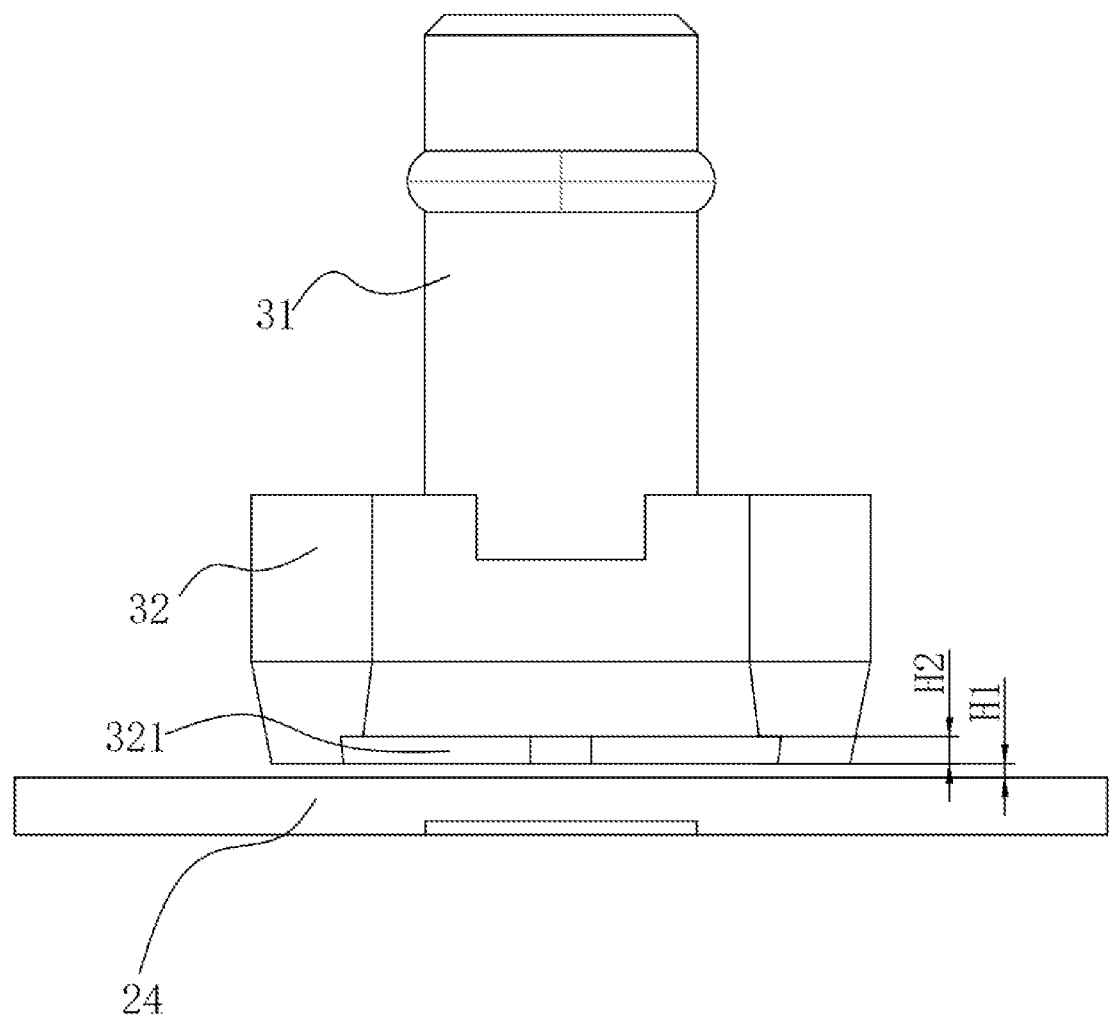
FIG. 3 is a diagram illustrating positional relationships of a liquid guide piece and an atomizing sheet of the atomizing module shown in FIG. 1.
Figure 4:
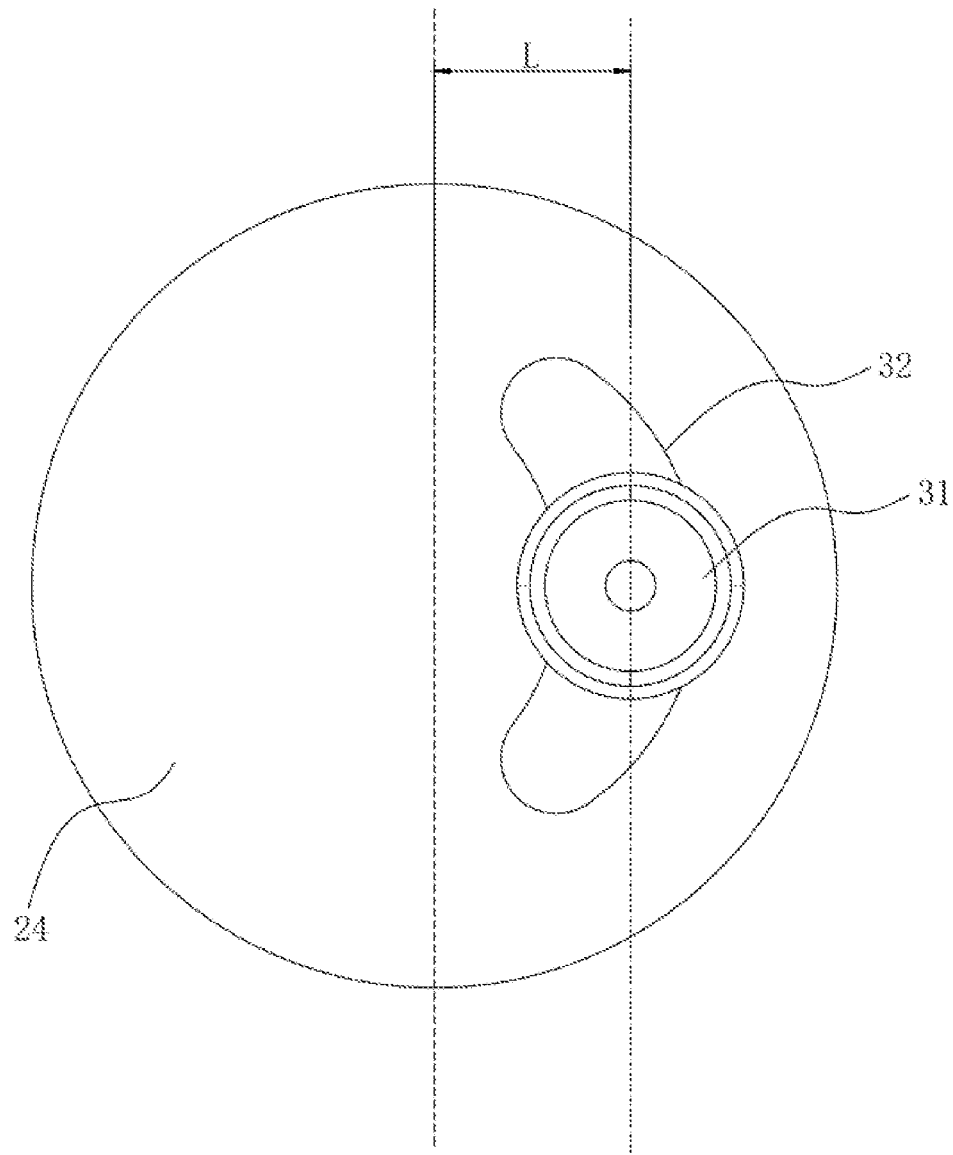
FIG. 4 is another diagram illustrating positional relationships of the liquid guide piece and the atomizing sheet of the atomizing module shown in FIG. 1.
Figure 5:
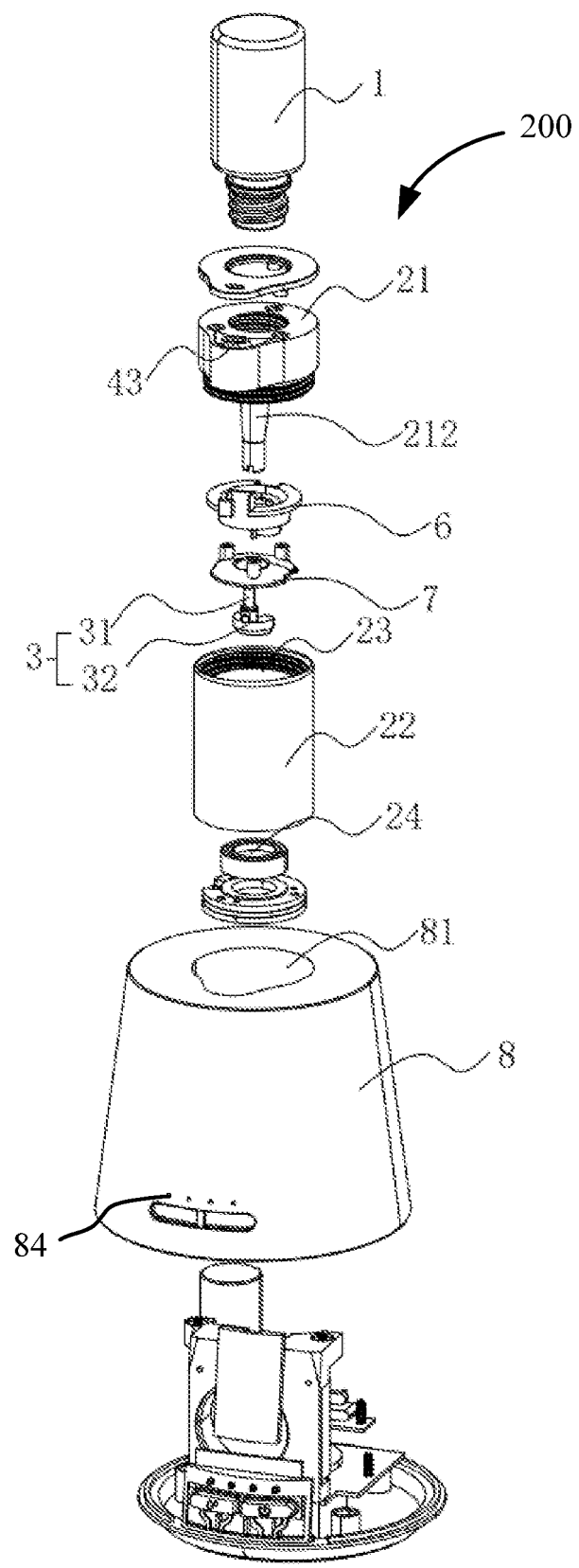
FIG. 5 is a schematic exploded diagram of a fragrance diffuser according to another embodiment of the present disclosure, the fragrance diffuser including the atomizing module according to the above embodiment.
Figure 6:
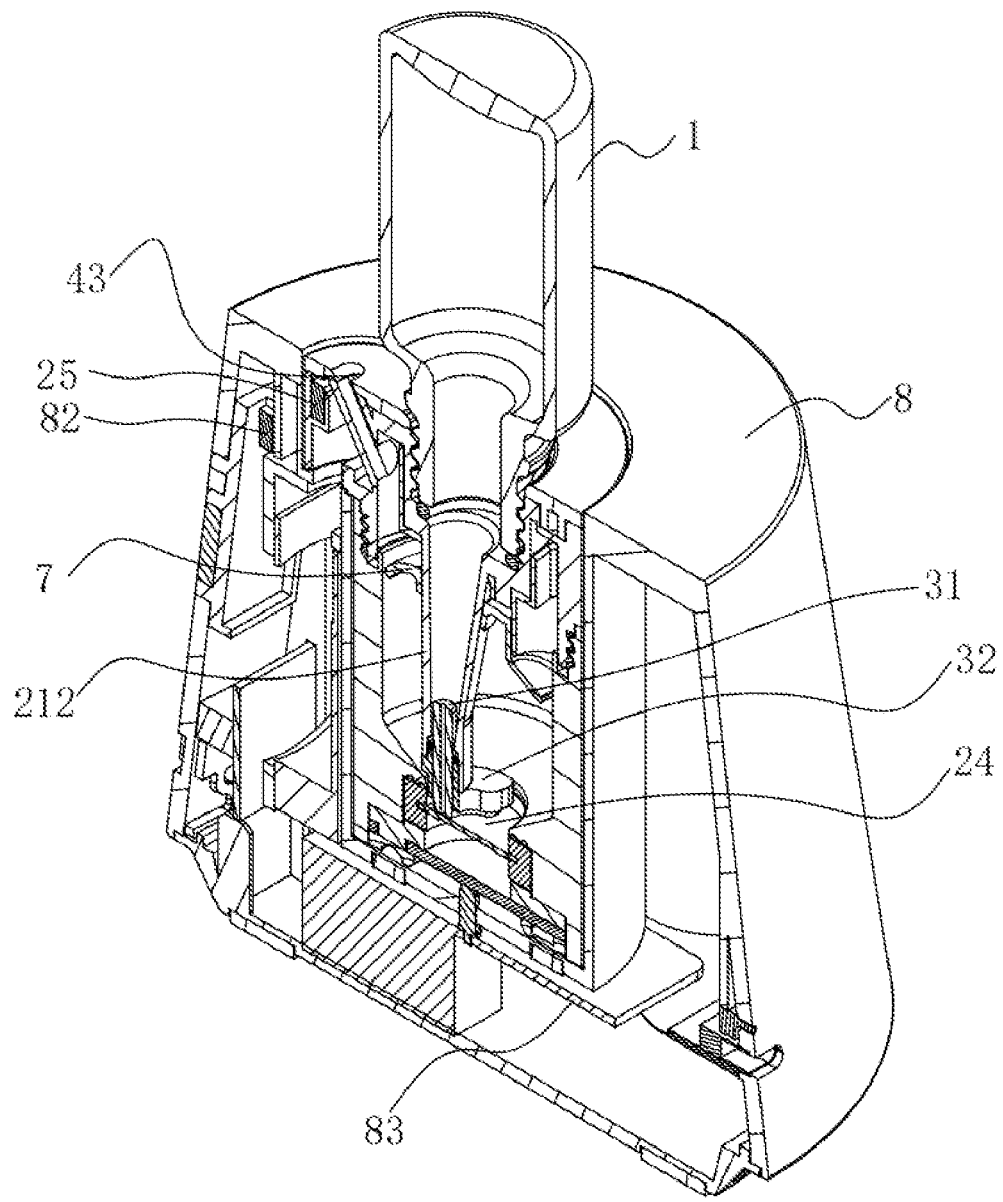
FIG. 6 is a schematic cross-sectional view of the fragrance diffuser shown in FIG. 5.
Figure 7:
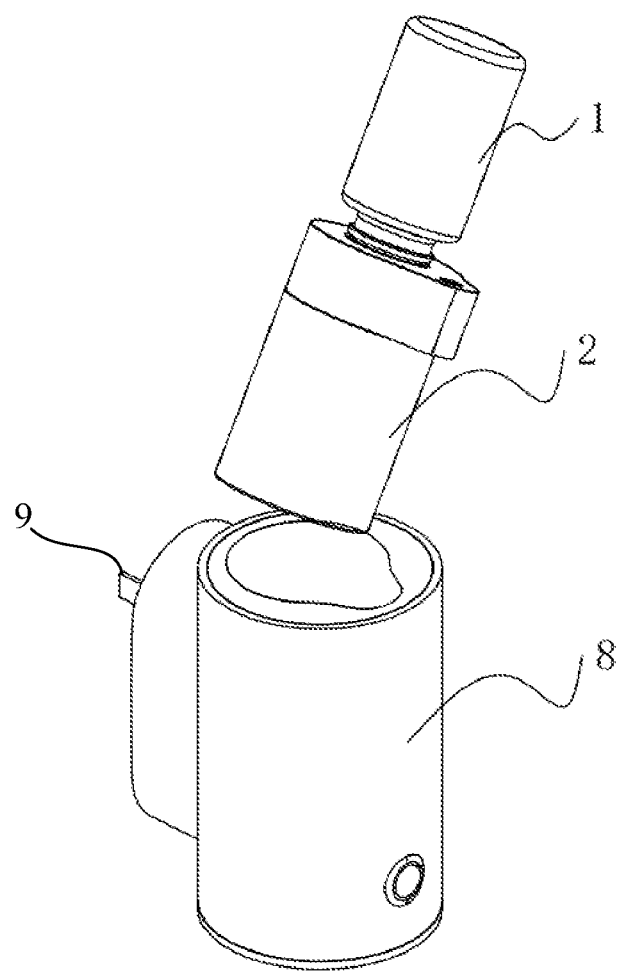
FIG. 7 is a schematic structural diagram of a fragrance diffuser according to some embodiments, and the fragrance diffuser is a wall plug-in fragrance diffuser.
Figure 8:
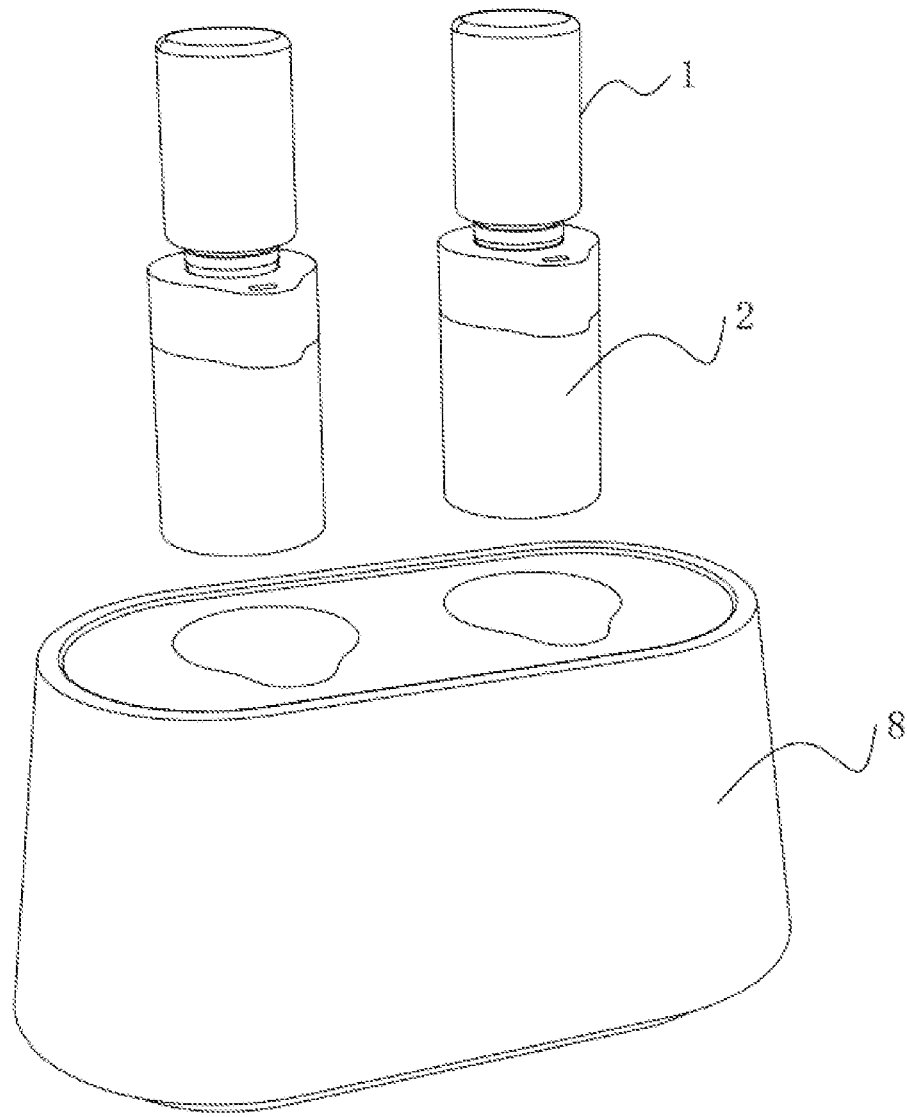
FIG. 8 is a schematic structural diagram of a fragrance diffuser according to some embodiments, and the fragrance diffuser includes two atomizing modules.
Figure 9:
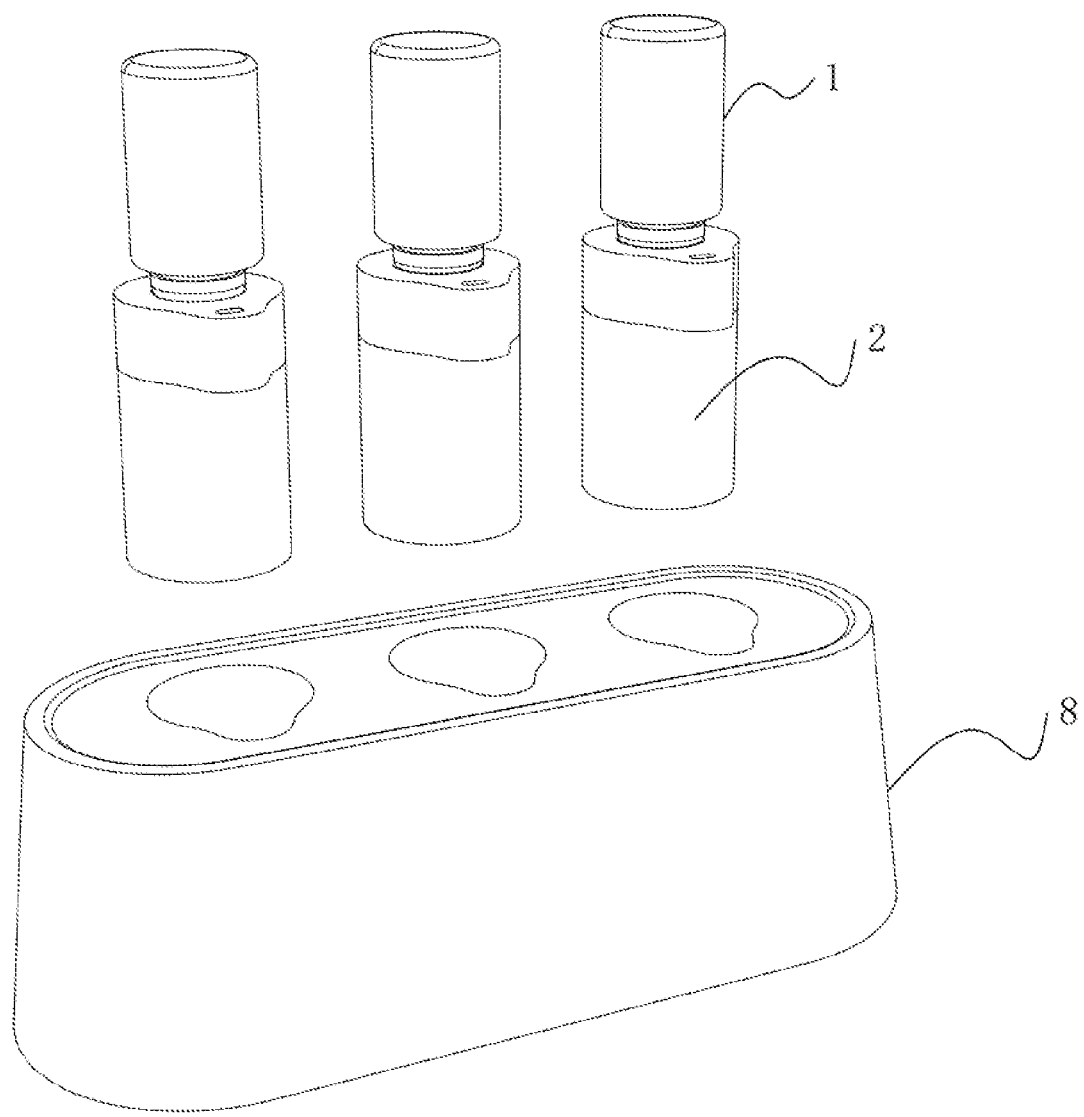
FIG. 9 is a schematic structural diagram of a fragrance diffuser according to some embodiments, and the fragrance diffuser includes three atomizing modules.

The present disclosure will be further explained with reference to FIG. 1 to FIG. 9 hereinafter.

Referring to FIG. 1 to FIG. 4 together, an embodiment of the present disclosure provides an atomizing module 100 capable of changing fluid speed, and the atomizing module 100 includes an atomizing housing 2, a liquid guide piece 3 and an atomizing sheet 24. The atomizing housing 2 includes a mounting part 211 and a buffering part 212, wherein the mounting part 211 is used to be connected with an external liquid bottle 1, the buffering part 211 is connected with the mounting part 212, the buffering part 212 defines a liquid buffering cavity 213, the atomizing housing 2 defines an air inlet channel 4, an atomizing cavity 23 and a mist outlet 43, wherein the air inlet channel 4 is used to be connected with an external ventilation device, the atomizing cavity 23 is in communication with the air inlet channel 4, the mist outlet 43 is in communication with the atomizing cavity 23, and the buffering part 211 extends into the atomizing cavity 23. The liquid guide piece 3 is arranged in the liquid buffering cavity 213 and located at one end of the buffering part 212 facing away from the mounting part 211, and the liquid guide piece 3 is used to slow down the dropping speed of liquid and control whether the liquid drops. The atomizing sheet 24 is located on one side of the liquid guide piece 3 facing away from the mounting part 211.

The external liquid bottle 1 is matched with the atomizing module 100 of the present disclosure in an inverted state to realize the atomization effect; if the liquid guide piece 3 is not provided, then the liquid will pour on the atomizing sheet 24 intensively and quickly under the action of gravity, and this will result in excessive essential oil covering on the atomizing sheet 24, thereby affecting the atomization effect; or this even results in excessive filling of essential oil in the atomizing cavity 23 such that the atomizing sheet 24 cannot perform atomization. After the liquid guide piece 3 is added, the dropping speed of liquid can be slowed down, and when there is too much liquid, the liquid can be controlled not to drop, thereby ensuring the best atomization effect in the whole atomization process.

In some embodiments, the liquid guide piece 3 includes a liquid guiding section 31 and a siphon section 32, the liquid guiding section 31 defines a liquid guiding through hole 311, the siphon section 32 defines a siphon groove 321, the siphon groove 321 is in communication with the liquid guiding through hole 311, the siphon section 32 abuts against the atomizing sheet 24, the siphon groove 321 faces the atomizing sheet 24, and when the liquid fully fills the siphon groove 321, the liquid in the liquid bottle 1 stops dropping.

When the liquid fully fills the siphon groove 321, there is no air between the siphon groove 321 and the liquid guiding through hole 311, and the liquid in the liquid buffering cavity 213 stops dropping onto the siphon groove 321 and the atomizing sheet 24; the atomizing sheet 24 can atomize the liquid normally under the conductive state, and when some liquid is atomized until the siphon groove 321 is not fully filled with the liquid, air will continue to flow into the space between the siphon groove 321 and the liquid guiding through hole 311, and the liquid in the liquid buffering cavity 213 will continue to drop onto the siphon groove 321 and the atomizing sheet 24 through the liquid guiding through hole 311. Therefore, through the ingenious design of mechanical structure, whether the liquid drops or not can be controlled.

In some embodiments, the siphon groove 321 has an arc-shaped cross section, the atomizing sheet 24 has a circular cross section, and the center position of the siphon groove 321 in the width direction is 2 to 10 mm away from the center position of the atomizing sheet 24.

By adopting the above technical solution, the optimal atomization area of the atomizing sheet 24 is generally the central area, and the liquid drops preferentially from the relatively central position in the siphon groove 321 through the liquid guiding through hole 311; if the centers of the siphon groove 321 and the atomizing sheet 24 are overlapped, then the atomization effect of the atomizing sheet 24 will be affected when the liquid drops, while the arrangement of the eccentric structure can effectively avoid the interference of liquid dropping with the atomization effect and achieve the optimal atomization effect.

In some embodiments, the atomizing module 100 further includes a first sealing ring 15, which is arranged at the joint of the liquid guide piece 3 and the buffering part 212, so as to prevent the liquid from leaking from the joint of the liquid guide piece 3 and the buffering part 212.

The atomizing module 100 further includes a second sealing ring 5 which is arranged on the mounting part 211, and the second sealing ring 5 is used for sealing the joint of the mounting part 211 and the external liquid bottle 1 when the mounting part 211 is connected with the external liquid bottle 1.

By adopting the above technical solution, the liquid guide piece 3 achieves the communication or isolation between the buffering part 212 and the atomizing cavity 213, the first sealing ring 15 prevents the liquid from leaking between the liquid guide piece 3 and the buffering part 212, and the second sealing ring 5 prevents the liquid from leaking between the mounting part 211 and the external liquid bottle 1, thereby ensuring the tightness of the atomizing module 100.

In some embodiments, the liquid guide piece 3 is made of a porous ceramic material or oil-conducting cotton or foamed silica gel or fiber.

By adopting the above technical solution, the dropping speed of liquid onto the atomizing sheet 24 can be slowed down more effectively.

In some embodiments, the atomizing housing 2 includes an upper atomizing housing 21 and a lower atomizing housing 22 which are detachably connected with each other, wherein the mounting part 211, the buffering part 212, the air inlet channel 4 and the mist outlet 43 are all arranged in the upper atomizing housing 211, and the atomizing cavity 23 and the atomizing sheet 24 are all arranged in the lower atomizing housing 22.

By adopting the above technical solution, the upper atomizing housing 21 and the lower atomizing housing 22 are detachably connected with each other, which is convenient for users to disassemble and clean the surface of the atomizing sheet 24 inside the lower atomizing housing 22, so as to prevent dirt generated by some liquid from affecting the atomization effect, or to prevent residual original liquid from affecting the atomization purity of the current liquid when the liquid to be atomized is changed.

In some embodiments, the atomizing module 100 further includes a blocking member 6, the blocking member 6 is located in the atomizing cavity 23 and close to the air inlet channel 4 and the mist outlet 43, and it is used for blocking large droplets of liquid.

By adopting the above technical solution, the large droplets of liquid that are not completely atomized are attached to the blocking member 6, and they can continue to fall back to the atomizing sheet 24 to be atomized again, thereby improving the atomization effect. In addition, it is also possible to avoid the accumulation of large droplets of liquid that are not completely atomized around the mist outlet 43, which otherwise would affect the mist releasing effect and the user experience.

In some embodiments, the air inlet channel 4 includes an air inlet 41 and an air outlet 42, and the atomizing module 100 further includes an airflow direction guide piece 7 which is arranged in the upper atomizing housing 21, the air inlet 41 and the air outlet 42 are respectively located on both sides of the guide piece 7, and the guide piece 7 is used for guiding the airflow from the air inlet 41 to the air outlet 42 to be released. Under the use state, the level of the air inlet 41 is higher than that of the air outlet 42, and the external airflow enters the air inlet channel 4 through the air inlet 41, and then flows to the atomizing cavity 23 through the air outlet 42.

By adopting the above technical solution, the flow direction of the airflow can be controlled, such that the airflow circulates for a full circle in the atomizing cavity 23 to drive atomized liquid micro-particles to be sent out from the mist outlet 43, thereby preventing the non-atomized liquid from colliding with the atomized liquid and achieving a better atomization effect.

The atomizing module 100 is especially suitable for the atomization of viscous liquid like pure essential oils, and such viscous liquid can form a liquid film on the surface of the atomizing sheet 24, such that the atomization efficiency of liquid is higher, and the atomization speed and atomization amount can be well controlled to avoid the waste of the liquid to be atomized.

Specifically, the upper atomizing housing 21 is provided with the mounting part 211 connected with the external liquid bottle 1, the mounting part 211 is provided with the second sealing ring 5, and when the mounting part 211 is connected with the external liquid bottle 1, the second sealing ring 5 seals the joint of the mounting part 211 and the external liquid bottle 1, so as to prevent liquid leakage at the joint of the external liquid bottle 1 and the mounting part 211 when liquid drops. The mounting part 211 may be connected with the external liquid bottle 1 through screw connection, snap connection, transition fit or the like.

The mounting part 211 is connected with the buffering part 212, the buffering part 212 defines a liquid buffering cavity 213 which is in communication with the external liquid bottle 1, and the liquid buffering cavity 213 has a funnel-shaped structure, that is, the opening of the external liquid bottle 1 is larger than the outlet of the liquid buffering cavity 213.

The lower atomizing housing 22 is provided therein with the atomizing cavity 23 and the atomizing sheet 24, the buffering part 212 extends into the atomizing cavity 23, the atomizing sheet 24 is located below the buffering part 212, and the liquid guide piece 3 is arranged on one side of the buffering part 212 facing the atomizing sheet 24.

To more effectively slow down the dropping speed of liquid onto the atomizing sheet 24, the liquid guide piece 3 may be made of a porous ceramic material, oil-conducting cotton, foamed silica gel or fiber, and the internal pore size, the number of pores, the shape of the porous structure or the like of the liquid guide piece 3 may be set as required according to the atomization requirements.

In order to make it convenient for the user to disassemble and clean the surface of the atomizing sheet 24 inside the lower atomizing housing 22 so as to prevent the dirt generated by some liquid from affecting the atomization effect, or to prevent the residual original liquid from affecting the atomization purity of the current liquid when the liquid to be atomized is changed, in this embodiment, the atomizing housing 2 includes the upper atomizing housing 21 and the lower atomizing housing 22 that are detachable, and the upper atomizing housing 21 and the lower atomizing housing 22 may be connected by screw connection, and of course, they may also be connected by snap connection or plugging connection.

It should be noted that, in some other embodiments, the atomizing housing 2 may also be integrally formed.

The liquid guide piece 3 includes a liquid guiding section 31 and a siphon section 32, wherein the liquid guiding section 31 defines a liquid guiding through hole 311, the siphon section 32 defines a siphon groove 321, and the siphon groove 321 is in communication with the liquid guiding through hole 311. The cross-sectional area of the liquid guiding through hole 311 should be less than 2.0 mm$^2$, and the liquid guiding through hole 311 is mainly used for ventilation in the liquid guiding process; if the area is too large, it is likely for the liquid to quickly drop on the atomizing sheet 24, which tends to cause liquid waste. The distance between one side of the siphon section 32 that is close to the atomizing sheet 24 and the atomizing sheet 24 is H1, which should be controlled at 0 to 0.5 mm, and the depth of the siphon groove 321 is H2, which should be controlled at 0.3 to 1.5 mm. In addition, the siphon groove 321 has an arc-shaped cross-section and the atomizing sheet 24 has a circular cross-section, and the distance between the center position of the siphon groove 321 in the width direction and the center position of the atomizing sheet 24 is L, which is 2 to 10 mm.

When the liquid fully fills the siphon groove 321, the liquid in the liquid bottle 1 stops dropping, and when the liquid fully fills the siphon groove 321, there is no air between the siphon groove 321 and the liquid guiding through hole 311, and the liquid in the liquid buffering cavity 213 stops dropping onto the siphon groove 321 and the atomizing sheet 24; the atomizing sheet 24 can atomize the liquid normally under the conductive state, and when some liquid is atomized until the siphon groove 321 is not fully filled with the liquid, air will continue to flow into the space between the siphon groove 321 and the liquid guiding through hole 311, and the liquid in the liquid buffering cavity 213 will continue to drop onto the siphon groove 321 and the atomizing sheet 24 through the liquid guiding through hole 311. Therefore, through the ingenious design of mechanical structure, whether the liquid drops or not can be controlled. If the siphon groove 321 is too small, a small amount of liquid will fully fill the whole siphon groove 321, and the amount of the liquid may even be insufficient for one time of atomization of the smallest unit for the atomization sheet 24; if the siphon groove 321 is too large, more liquid will be needed in order to prevent the liquid from continuously dropping, and the liquid may overflow the atomizing sheet 24 to affect the whole atomization work. As such, the selection of H1 and H2 in the present disclosure can prevent both insufficient and excessive dropping of the liquid. In addition, since the position of the atomizing sheet 24 with the best atomization effect is located at the center of the atomizing sheet 24, the position at which oil is guided from the porous ceramic to the atomizing sheet 24 is deliberately set to deviate from the center of the atomizing sheet 24 by a deviation distance of L, so as to prevent the atomization effect from being affected by covering the best atomization position of the atomizing sheet 24.

The joint between the liquid guide piece 3 and the buffering part 212 is provided with the first sealing ring 15 to prevent liquid leakage at the joint, and the first sealing ring 15 can prevent the liquid from leaking between the liquid guide piece 3 and the buffering part 212 and ensure the tightness of the atomizing module 100.

The upper atomizing housing 21 further defines an air inlet channel 4 which includes an air inlet 41 and an air outlet 42, wherein the air inlet 41 is used to be connected with an external ventilation device, and the air outlet 42 is used for communication with the atomizing cavity 23.

The upper atomizing housing 21 further defines a mist outlet 43 that is in communication with the atomizing cavity 23, and the mist outlet 43 is not directly in communication with the air inlet 41.

The airflow direction guide piece 6 guides the airflow from the air inlet 41 to the air outlet 42 to be released, the level of the air inlet 41 relative to the horizon is higher than the level of the air outlet 42, the air inlet 41 and the air outlet 42 are respectively located on both sides of the airflow direction guide piece 6, and the airflow direction guide piece 6 guides the airflow to flow in the designated circumferential direction within the air inlet channel 4, such that the airflow circulates for a full circle in the atomizing cavity 23 to drive atomized liquid micro-particles to be sent out from the mist outlet 43, thereby preventing the non-atomized liquid from colliding with the atomized liquid and achieving a better atomization effect, and further preventing the backflow of mist or liquid.

The upper atomizing housing 21 is provided therein with a blocking member 7 which has a generally umbrella-like structure, the blocking member 7 is fixedly sleeved on the buffering part 212 and is located in the atomizing cavity 23 near the air inlet channel 4 and the mist outlet 43, and it is mainly used for blocking large droplets of liquid that are not completely atomized.

Working principle is described as follows:

The external liquid bottle 1 is screwed on the upper atomizing housing 21 upside down, and a second sealing ring 5 is arranged at the joint between the external liquid bottle 1 and the upper atomizing housing 21 to prevent the liquid of the external liquid bottle 1 from leaking from the joint therebetween.

Under the action of gravity, the liquid in the external liquid bottle 1 passes through the liquid buffering cavity 213, the liquid guiding section 31 and the siphon section 32, and the first sealing ring 15 is arranged at the joint between the liquid guide piece 3 and the buffering part 212 to prevent the liquid from leaking from the joint therebetween, and thus liquid leakage between the liquid guide piece 3 and the buffering part 212 can be prevented.

The liquid to be atomized drops from the siphon groove 321 onto the atomizing sheet 24, and the atomizing sheet 24 can normally atomize the liquid under the conductive state; when the siphon groove 321 is not fully filled with the liquid to be atomized, air will continue to flow into the space between the siphon groove 321 and the liquid guiding through hole 311, and the liquid in the liquid buffering cavity 213 will continue to drop onto the siphon groove 321 and the atomizing sheet 24 through the liquid guiding through hole 311; when the liquid to be atomized fully fills the siphon groove 321, there is no air between the siphon groove 321 and the liquid guiding through hole 311, and the liquid stops dropping; if the atomizing sheet 24 is still in the conductive state, the atomization will be continued; and if the atomizing sheet 24 is not powered, the whole liquid will not drop again, and thus there is no need to worry that the liquid in the inverted external liquid bottle 1 will overflow the atomizing sheet 24.

The airflow direction guide piece 6 guides the airflow to flow in the designated circumferential direction within the air inlet channel 4, such that the airflow circulates for a full circle in the atomizing cavity 23 to drive the atomized liquid and send it out from the mist outlet 43; and the blocking member 7 is located in the atomizing cavity 23 near the air inlet channel 4 and the mist outlet 43, and is used to block the large droplets of liquid that are not completely atomized.

In some other embodiments, the liquid guide piece 3 may also be provided with a floating sealing structure at one side close to the atomizing sheet 24; that is, when the liquid drops excessively, a floating ball floats to block the liquid guiding through hole 311 to achieve the effect of preventing the liquid from continuing to drop.

Referring to FIG. 5 and FIG. 6 together, another embodiment of the present disclosure provides a fragrance diffuser 200, which is especially suitable for the atomization and aromatherapy of viscous liquid like pure essential oils, and the fragrance diffuser 200 can control the atomization speed and avoid the waste of the liquid to be atomized. The fragrance diffuser 200 includes a host housing 8, a micro blower, an electric control main board 83 and the atomizing module 100 of the above embodiment, wherein the host housing 8 defines a host chamber 81, the atomizing module 100 is arranged in the host chamber 81, the micro blower and the electric control main board 83 are both arranged in the host housing 8, an air outlet of the micro blower is in communication with the air inlet 41 of the air inlet channel 4, the electric control main board 83 is electrically connected with the atomizing sheet 24, and the electric control main board 83 is configured to control the atomizing sheet 24 to atomize the liquid.

By adopting the above technical solution, the atomizing module 100 of the present disclosure is especially suitable for the atomization of pure essential oil; since pure essential oils is a liquid with higher viscosity, only a thin layer of essential oil can be covered on the surface of the atomizing sheet 24 during atomization, so it is especially necessary to control the dropping speed and droplet size of essential oil; therefore, the atomization effect can be optimally realized by the cooperation of the atomizing module 100 and the fragrance diffuser 200.

In some embodiments, the host housing 8 is detachably connected with the atomizing module 100.

By adopting the above technical solution, since both the atomizing module 100 and the host housing 8 are independent structures, water will not enter the atomizing module 100 or the host of the fragrance diffuser 200 during cleaning, thereby preventing the atomizing module 100 or the host from being damaged.

In some embodiments, the main housing 8 is provided with at least two host chambers 81, and each of the host chambers 81 accommodates one corresponding atomizing module 100.

By adopting the above technical solution, one fragrance diffuser 200 can simultaneously perform fragrance diffusion on multiple kinds of liquid.

In some embodiments, the fragrance diffuser 200 includes a magnet 25, a Hall inductive probe 82 and an indicator lamp 84, wherein the magnet 25 is arranged in the atomizing housing 2, the Hall inductive probe 82 is arranged in the host housing 8, and the position of the Hall inductive probe 82 corresponds to that of the magnet 25; the indicator lamp 84 is arranged on the atomizing housing 2 and/or the host housing 8, and both the Hall inductive probe 82 and the indicator lamp 84 are electrically connected with the electric control main board 83.

By adopting the above technical solution, when the atomizing module 100 is connected with the host housing 8, the Hall inductive probe 82 interacts with the magnet 25, the Hall inductive probe 82 will send out a signal, and after the signal is detected by the electric control main board 83, the electric control main board 83 starts to drive the atomizing sheet 24 to operate such that the atomizing sheet 24 starts to atomize the liquid. In addition, when the electric control main board 83 performs atomization, the indicator lamp 84 starts to light up, which indicates that atomization is in progress.

It shall be appreciated, in some other embodiments, the Hall inductive probe 82 may be arranged in the atomizing housing 2, the magnet 25 is arranged in the host housing 8, and the position of the Hall inductive probe 82 corresponds to that of the magnet 25; when the atomizing module 100 is placed in the host chamber 81, the Hall inductive probe 82 is electrically connected with the electric control main board 83.

The fragrance diffuser 200 of this embodiment may be placed on a plane such as a desktop or the ground for use, or it may be plugged into a wall socket for use. For example, referring to FIG. 7, in one embodiment, the fragrance diffuser 200 includes a plug 9, which is arranged on the side wall of the host housing 8, and during use, the plug 9 is plugged into the wall socket such that the fragrance diffuser 200 can be powered on and the fragrance diffuser 200 can be used after it is turned on. With this arrangement, the fragrance diffuser 200 of this embodiment will occupy the space on the desktop or the ground during use.

It shall be noted here that one or more host chambers 81 may be arranged in the host housing 8, and when multiple chambers 81 are arranged, one atomizing module 100 may be placed in each host chamber 81, and thus one fragrance diffuser 200 can simultaneously aromatize multiple kinds of liquid to prepare a more comprehensive fragrance effect. For example, FIG. 8 and FIG. 9 respectively disclose embodiments in which two or three atomizing modules are arranged in one host housing 8.

The atomizing module 100 of the above embodiment is detachably connected in the host chamber 81, and the specific detachable connection mode may be screw connection, plugging connection, snap connection, sliding connection of guide rail and guide groove or the like. Since the atomizing module 100 and the host housing 8 are all independent structures, water will not enter the atomizing module 100 or the host during cleaning, thereby preventing the atomizing module or the host from being damaged.

The host housing 8 is provided therein with a micro blower and an electric control main board 83 for controlling the atomizing sheet 24 to perform atomization, an air outlet of the micro blower is in communication with the air inlet 41 of the air inlet channel 4, and the electric control main board 83 is electrically connected with the atomizing sheet 24.

A magnet 25 is arranged in the atomizing housing 2, a Hall inductive probe 82 is arranged in the host housing 8 at the position corresponding to the magnet 25, an indicator lamp 84 is arranged on the atomizing housing 2 or the host housing 8, and both the Hall inductive probe 82 and the indicator lamp 84 are electrically connected with the electric control motherboard 83.

It shall be noted here that the circuit structure of the electric control main board 83 does not belong to the innovative point of the present disclosure, the circuit may also adopt a conventional atomization circuit module, and the Hall inductive probe 82 and the indicator lamp 84 may be connected with the electric control main board 83 simply by flexible wires, all of which belong to the prior art and thus will not be further described herein.

The specific working process is as follows:

After the liquid bottle 1 is screwed into the upper atomizing housing 21 through the threaded bottle opening, the liquid enters the liquid buffering cavity 213 under the action of gravity, and the liquid in the liquid buffering cavity 213 drops onto the surface of the atomizing sheet 24 through the liquid guide piece 3; when the atomizing module 100 is placed within the host chamber 81 in the host housing 8, the power supply is connected, and the connecting electrode on the atomizing module 100 are in contact and electrically connected with the connecting electrode in the host housing 8; at the same time, the Hall inductive probe 82 interact with the magnet 25, the Hall inductive probe 82 detects the signal and transmits it to the electric control main board 83, and after receiving the signal, the electric control main board 83 starts to drive the atomizing sheet 24 to start working and atomize the liquid. At the same time, the micro blower in the host blows airflow into the air inlet channel 4 in the atomizing module 100, and sends out the mist generated after the atomization of essential oil from the mist outlet 43.

The above-mentioned embodiments are only exemplary embodiments of the present disclosure, and the scope claimed in the present disclosure shall not be limited thereto, and any insubstantial change and substitution made by those skilled in the art on the basis of the present disclosure shall belong to the scope claimed in the present disclosure.

What is claimed is:

1. An atomizing module capable of changing fluid speed, comprising:
    an atomizing housing, comprising a mounting part and a buffering part, the mounting part configured to be connected with an external liquid bottle, the buffering part connected with the mounting part, the buffering part defining a liquid buffering cavity, the atomizing housing defining an air inlet channel, an atomizing cavity and a mist outlet, the air inlet channel configured to be connected with an external ventilation device, the atomizing cavity being in communication with the air inlet channel, the mist outlet being in communication with the atomizing cavity, and the buffering part extending into the atomizing cavity;
    a liquid guide piece arranged in the liquid buffering cavity and located at one end of the buffering part facing away from the mounting part, and the liquid guide piece configured to slow down a dropping speed of liquid and control whether the liquid drops; and
    an atomizing sheet located on one side of the liquid guide piece facing away from the mounting part.

2. The atomizing module of claim 1, wherein the liquid guide piece comprises a liquid guiding section and a siphon section, the liquid guiding section defines a liquid guiding through hole, the siphon section defines a siphon groove, the siphon groove is in communication with the liquid guiding through hole, the siphon section abuts against the atomizing sheet, and the siphon groove faces the atomizing sheet.

3. The atomizing module of claim 2, wherein a cross-section of the siphon groove is arc-shaped, a cross-section of the atomizing sheet is circular in shape, and a center position of the siphon groove in a width direction is 2 to 10 mm away from a center position of the atomizing sheet.

4. The atomizing module of claim 2, wherein an area of a cross-section of the liquid guiding through hole is less than 2.0 mm$^2$.

5. The atomizing module of claim 4, wherein a distance between one side of the siphon section that is close to the atomizing sheet and the atomizing sheet is 0 to 0.5 mm.

6. The atomizing module of claim 5, wherein a depth of the siphon groove is 0.3 to 1.5 mm.

7. The atomizing module of claim 1, wherein the liquid guide piece is made of a porous ceramic material, oil-conducting cotton, foamed silica gel or fiber.

8. The atomizing module of claim 1, wherein the atomizing module further comprises a first sealing ring, the first sealing ring is arranged at a joint of the liquid guide piece and the buffering part, so as to prevent the liquid from leaking from the joint of the liquid guide piece and the buffering part.

9. The atomizing module of claim 1, wherein the atomizing module further comprises a second sealing ring, the second sealing ring is arranged on the mounting part, and the second sealing ring is configured to seal a joint of the mounting part and the external liquid bottle when the mounting part is connected with the external liquid bottle.

10. The atomizing module of claim 1, wherein the liquid buffering cavity is funnel-shaped.

11. The atomizing module of claim 1, wherein the atomizing housing comprises an upper atomizing housing and a lower atomizing housing, the upper atomizing housing and the lower atomizing housing are detachably connected with each other, all of the mounting part, the buffering part, the air inlet channel and the mist outlet are arranged in the upper atomizing housing, and the atomizing cavity and the atomizing sheet are both arranged in the lower atomizing housing.

12. The atomizing module of claim 1, wherein the atomizing module further comprises a blocking member, the blocking member is located in the atomizing cavity and close to the air inlet channel and the mist outlet, and the blocking member is configured to block large droplets of liquid.

13. The atomizing module of claim 12, wherein the blocking member is umbrella-like shaped, and the blocking member is sleeved on the buffering part and is located in the atomizing cavity near the air inlet channel and the mist outlet.

14. The atomizing module of claim 1, wherein the air inlet channel comprises an air inlet and an air outlet;
the atomizing module further comprises an airflow direction guide piece, the airflow direction guide piece is arranged in the atomizing housing, the air inlet and the air outlet are respectively located on two sides of the guide piece, and the guide piece is configured to guide an airflow from the air inlet to the air outlet to be released, and in a use state, a level of the air inlet is higher than a level of the air outlet.

15. A fragrance diffuser, comprising a host housing, a micro blower, an electric control main board and the atomizing module of claim 1, wherein the host housing defines a host chamber, the atomizing module is arranged in the host chamber, the micro blower and the electric control main board are both arranged in the host housing, an air outlet of the micro blower is in communication with the air inlet of the air inlet channel, the electric control main board is electrically connected with the atomizing sheet, and the electric control main board is configured to control the atomizing sheet to atomize the liquid.

16. The fragrance diffuser of claim 15, wherein the host housing is detachably connected with the atomizing module.

17. The fragrance diffuser of claim 15, wherein the main housing defines at least two host chambers, and each of the at least two host chambers accommodates one corresponding atomizing module.

18. The fragrance diffuser of claim 15, wherein the fragrance diffuser comprises a magnet and a Hall inductive probe, the magnet is arranged in the atomizing housing, the Hall inductive probe is arranged in the host housing, a position of the Hall inductive probe corresponds to a position of the magnet, and the Hall inductive probe is electrically connected with the electric control main board.

19. The fragrance diffuser of claim 15, wherein the fragrance diffuser comprises a magnet and a Hall inductive probe, the Hall inductive probe is arranged in the atomizing housing, the magnet is arranged in the host housing, a position of the Hall inductive probe corresponds to a position of the magnet, and the Hall inductive probe is electrically connected with the electric control main board.

20. The fragrance diffuser of claim 15, wherein the fragrance diffuser comprises an indicator lamp, the indicator lamp is arranged on the atomizing housing and/or the host housing, and the indicator lamp is electrically connected with the electric control main board.

\* \* \* \* \*